United States Patent [19]

Burton et al.

[11] 4,160,086
[45] * Jul. 3, 1979

[54] 3-HETEROCYCLICTHIO-7-α-CARBOXY 2-ARYL ACETAMIDO CEPHALOSPORANIC ACID

[75] Inventors: George Burton, Coulsdon; Elzbieta Watson, Carshalton, both of England

[73] Assignee: Beecham Group Limited, England

[*] Notice: The portion of the term of this patent subsequent to Nov. 23, 1993, has been disclaimed.

[21] Appl. No.: 566,060

[22] Filed: Apr. 8, 1975

[30] Foreign Application Priority Data

Apr. 27, 1974 [GB] United Kingdom ............... 18557/74
Jul. 25, 1974 [GB] United Kingdom ............... 32806/74

[51] Int. Cl.² ........................................... C07D 501/36
[52] U.S. Cl. ......................................... 544/26; 544/27

[58] Field of Search ................ 260/243 C; 544/26, 27

[56] References Cited

U.S. PATENT DOCUMENTS

| 3,516,997 | 6/1970 | Takano et al. ................... 260/243 C |
| 3,635,961 | 1/1972 | Butler ............................... 260/243 C |
| 3,993,758 | 11/1976 | Burton et al. ........................... 544/26 |

Primary Examiner—Donald G. Daus
Assistant Examiner—David E. Wheeler
Attorney, Agent, or Firm—Jacobs & Jacobs

[57] ABSTRACT

A class of α-carboxy-3-heterocyclicthio cephems have an unusually high level of antibacterial activity against a wide variety of Gram-positive and Gram-negative organisms.

10 Claims, No Drawings

3-HETEROCYCLICTHIO-7-α-CARBOXY 2-ARYL ACETAMIDO CEPHALOSPORANIC ACID

This invention relates to a small group of cephalosporin compounds which we have found to have an unusually high level of antibacterial activity against a wide variety of Gram-positive and Gram-negative organisms. Such compounds are therefore of value as antibacterial agents in human beings and in farmyard animals and poultry.

According to the present invention there is provided a compound of formula (I) or a pharmaceutically acceptable salt or 4-carboxylic acid mono-ester thereof:

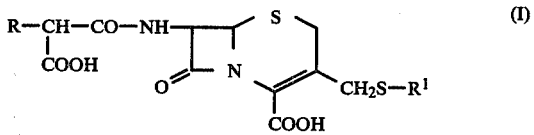

wherein R is a 2- or 3-thienyl group or a phenyl, 4-hydroxyphenyl, 3-chloro-4-hydroxyphenyl, 3,4-dihydroxyphenyl, or cyclohexa-1,4-dienyl group and $R^1$ represents a thiadiazolyl group, a triazolyl group or a tetrazolyl group, any of which may be substituted by a lower alkyl, trifluoromethyl, or carboxymethyl group.

Preferably R is a 2- or 3-thienyl or phenyl group, and most suitably $R^1$ represents a 1,3,4-thiadiazolyl; 1,2,3-triazolyl; or 1,2,3,4-tetrazolyl group; optionally substituted by lower alkyl or trifluoromethyl. Particular groups include the 2-methyl-1,3,4-thiadiazol-5-yl group; the 1-methyl-1H-tetrazol-5-yl group; the 1,2,3-triazol-4-yl group; the 4-methyl-1,2,3-triazol-5-yl group; or the 1-methyl-1,2,3-triazol-5-yl group. Other advantageous $R^1$ groups include 1,2,4-triazol-3-yl and 1-carboxymethyl-1H-tetrazol-5-yl.

The compounds of the present invention include the pharmaceutically acceptable 4-carboxylic acid mono-esters of compounds (I). Suitable esters include those which break down readily in the human body to leave the parent acid, for example acyloxyalkyl esters such as acetoxymethyl, pivaloyloxymethyl, α-acetoxyethyl, α-acetoxybenzyl and α-pivaloyloxyethyl esters. Other suitable esters include lactone, thiolactone and dithiolactone esters (i.e. ester groups of formula:

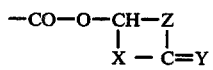

wherein X and Y are oxygen or sulphur and Z is a divalent hydrocarbon group) especially the phthalidyl and substituted phthalidyl esters, e.g. 3,4-dimethoxyphthalidyl ester.

Examples of the compounds of formula (I) include the mono and bis sodium and potassium salts, but others are also useful, e.g. calcium, magnesium and aluminium salts, and ammonium or substituted ammonium salts for example those with trialkylamines such as triethylamine, procaine, dibenzylamine, triethanolamine, 1-ephenamine, ethylpiperidine and other amines which have been used to form salts with benzylpenicillin. When the 4-carboxyl group is esterified, it is of course still possible to prepare salts at the α-carboxy group.

Particular compounds of this invention include:

7-(α-carboxythien-3-ylacetamido)-3-(2-methyl-1,3,4-thiadiazol-5-ylthio)methylceph-3-em-4-carboxylic acid;

7-(α-carboxythien-3-ylacetamido)-3-(1-methyl-1H-tetrazol-5-ylthio)methylceph-3-em-4-carboxylic acid;

7-(α-carboxyphenylacetamido)-3-(1-methyl-1H-tetrazol-5-ylthio)methylceph-3-em-4-carboxylic acid;

7-(α-carboxythien-2-ylacetamido)-3-(1-methyl-1H-tetrazol-5-ylthio)methylceph-3-em-4-carboxylic acid;

7-(α-carboxythien-3-ylacetamido)-3-(1H-1,2,4-triazol-3-ylthio)methylceph-3-em-4-carboxylic acid;

7-(α-carboxythien-3-ylacetamido)-3-(1-carboxymethyl-1H-tetrazol-5-ylthio)methylceph-3-em-4-carboxylic acid.

Compounds of formula (I), salts and esters thereof may be prepared by reacting a compound of formula (II):

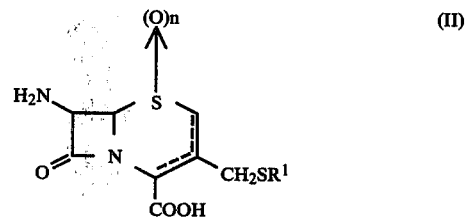

or a salt, ester or silyl derivative thereof, wherein n is 0 or 1, the dotted line represents a bond in the 2- or 3-position, and $R^1$ is as defined in formula (I) with an N-acylating derivative of an acid of formula (III):

wherein R is as defined in formula (I) and X is a carboxylic acid group, a halocarbonyl group, e.g. a chlorocarbonyl group, or a blocked carboxylic acid group, and thereafter removing the carboxylic acid blocking group, if present, and, if necessary, carrying out one or more of the following steps:

(i) converting a Δ2 isomer to a Δ3 isomer;

(ii) removing any silyl groups by alcoholysis or hydrolysis;

(iii) reducing a sulphoxide compound to form the desired sulphide compound.

By the term "silyl derivative" of compound (II) we mean the product of the reaction between compound (III) and a silylating agent such as a halodialkylsilane, a halotrialkylsilane, a halodialkoxysilane or a halotrialkoxysilane, or a corresponding aryl or aralkylsilane and compounds such as hexamethyldisilazane. The preferred silylating agent is trimethylchlorosilane.

Suitable N-acylating derivatives of the acid (III) include the acid chloride, bromide, anhydride, mixed anhydride, and the reactive intermediates formed from the acid and a carbodiimide or carboxyldimidazole. Another special N-acylating derivative of the acid (III) is the Ketone (IV):

although in such cases the group X should be a halocarbonyl group, especially the chlorocarbonyl group. Yet another group of N-acylating agents of the acid (III) include activated esters. Such activated esters, for example the ester formed with 1-hydroxybenzotriazole or, preferably, N-hydroxysuccinimide, may be prepared in situ by the reaction of the acid (III) with the appropriate hydroxy compound in the presence of a carbodiimide, preferably dicyclohexylcarbodiimide.

When the compound resulting after N-acylation contains a sulphoxide group at the 1-position, this may be reduced by conventional methods, e.g. with triphenylphosphine and acetyl chloride. When the resultant compound is a Δ2 isomer, the desired Δ3 isomer may be obtained by treatment of the former with a base, e.g. an alkali metal hydroxide or tertiary amine base such as pyridine or triethylamine. The method used to remove any carboxyl blocking groups in the side chain will depend on the identity of the blocking group. Many esters are suitable as blocked carboxyl groups and these may be hydrolysed to the free acid by base—or acid catalysed hydrolysis or by enzymic hydrolysis. However, to minimise isomerisation and side reactions aqueous solvents are better avoided and Lewis acids or reducing systems such as zinc-acetic acid, or catalytic hydrogenation may be preferable as means of de-esterification.

Compounds of formula (I) may also be prepared by reaction of a compound of formula (V) or a salt or ester derivative thereof:

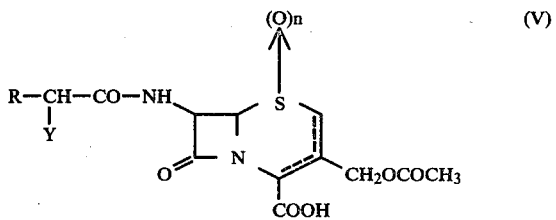

wherein Y is a carboxylic acid group or a salt thereof, or a blocked carboxylic acid group, R is as defined in formula (I), n is 0 or 1 and the dotted line represents a bond in the 2- or 3-position, with a thiol of formula $R^1SH$ wherein $R^1$ is as defined in formula (I), followed, if necessary, by the removal of the blocking group from the blocked carboxyl group Y and, if necessary, by one or both of the following steps:

(i) converting a Δ2 isomer to a Δ3 isomer;

(ii) reducing the sulphoxide compound to the desired sulphide compound.

Methods for isomerisation from Δ2 to Δ3 and reduction of sulphoxides are as described earlier. The remarks made above about carboxyl blocking groups and their removal to produce the free acid also apply in this case.

The following Examples illustrate the preparation of some of the compounds of this invention.

EXAMPLE 1

(a) Sodium 7-(α-phenoxycarbonylthien-3-ylacetamido)-3-(2-methyl 1,3,4-thiadiazol-5-ylthio)methylceph-3-em-4-carboxylate α-(phenoxycarbonyl)thien-3-ylacetyl chloride (0.01 M) in anhydrous acetone (25 ml.) was added to an ice bath cooled solution of 7-amino-3-(2-methyl-1,3,4-thiadiazol-5-yl-thio)methylceph-3-em-4-carboxylic acid (0.01 M) and triethyl-amine (3.0 ml.) in acetone (25 ml.) and water (50 ml.). The solution was stirred at room temperature for 3 hours, the acetone was removed in vacuo and the aqueous residue was diluted with water. The aqueous solution was covered with ethyl acetate (50 ml.), acidified to pH 1.5 with 1 N HCl, the organic phase was separated off and the aqueous layer was extracted with ethyl acetate (50 ml.). The combined extracts were washed with water (2×50 ml.) and brine (50 ml.), dried over anhydrous magnesium sulphate, treated with 2 N sodium 2-ethylhexoate in methyl isobutyl ketone (1.5 ml.) and diluted with anhydrous ether (100 ml.). The precipitated sodium salt was collected, washed with anhydrous ether and dried in vacuo.

Yield 29.5%; N.m.r. spectrum $[(CD_3)_2SO]$ δ=9.8-9.4 (1H,m, —NH—), 7.7-7.0 (8H,m aromatic and thienyl protons), 5.8-5.3 (1H,m, $C_7$ proton), 5.40 (1H,s, α-proton), 5.2-4.9 (1H,m, $C_6$ proton), 4.8-4.0 (2H,m, —$CH_2S$—), 4.0-3.1 (2H,m, $C_2$ methylene protons), 2.67 (3H,m, thiadiazole methyl protons); u.v. spectrum (95% ethanol), λmax 274 nm (ε=14 640). Paper chromatography showed a zone at $R_f$=0.67.

(b) 7-(α-Carboxythien-3-ylacetamido)-3-(2-methyl-1,3,4-thiadiazol-5-ylthio)methylceph-3-em-4-carboxylic acid disodium salt Sodium 7-(α-phenoxycarbonylthien-3-ylacetamido)-3-(2-methyl-1,3,4-thiadiazol-5-ylthio)methylceph-3-em-4-carboxylate (1.37 g., 0.0023 M) dissolved in water (50 ml.) was treated with sodium tetraborate (1.65 g., 0.0046 M) and stirred at room temperature for three hours. The solution was then acidified to pH 4 (1 N hydrochloric acid) in the presence of ethyl acetate (50 ml.). The organic layer was discarded. The solution was then acidified to pH 1.5 (1 N hydrochloric acid) in the presence of methylisobutylketone (25 ml.), and extracted with a further portion of methylisobutylkentone (25 ml.).

The methylisobutylketone was extracted to pH 7 with 0.5 N sodium bicarbonate and the extracts freeze dried, after washing with ether (25 ml.), to give the di-sodium salt of the product 0.84 g., 67.4% yield.

U.V. Spectrum (95% ethanol) λmax 277 nm (ε=12,470). Paper chromatography (butanol/ethanol/water) showed a zone at $R_f$=0.07.

EXAMPLE 2

(a) Sodium 7-(α-phenyoxycarbonylthien-3-ylacetamido)-3-(1-methyl-1H-tetrazol-5-ylthio)methylceph-3-em-4-carboxylate α-(Phenoxycarbonyl)thien-3-ylacetyl chloride was reacted with 7-amino-3-(1-methyl-1H-tetrazol-5-ylthio)methylceph-3-em-4-carboxylic acid as described in Example 1. Yield 22.1%; N.m.r. spectrum $[(CD_3)_2SO]$,=9.8-9.5 (1H,m, —NH—), 7.7-7.0 (8H,m, aromatic and thienyl protons), 5.8-5.3 (1H,m, $C_7$ proton), 5.40 (1H,s, α proton), 5.2-4.9 (1H,m, $C_6$ proton), 4.7-4.1 (2H,m, —$CH_2S$—), 3.95 (3H,s, tetrazole methyl protons), 4.0-3.1. (2H,m, $C_2$ methylene protons); u.v. spectrum (95% ethanol), λmax 268 nm (ε=9,700). Paper chromatography showed a zone at $R_f$=0.59.

(b)

7-(α-Carboxythien-3-ylacetamido)-3-(1-methyl-1H-tetrazol-5-ylthio)methyl ceph-3-em-4-carboxylic acid disodium salt

Sodium 7-(α-phenoxycarbonylthien-3-ylacetamido)-3-(1-methyl-1H-tetrazol-5-ylthio)methylceph-3-em-4-carboxylate (1.0 g., 0.0017 M) was treated with sodium tetraborate (1.3 g., 0.0034 M), as described in Example 1, to give the di-sodium salt of the product 0.57 g., 62.3% yield. u.v. spectrum (95% ethanol), λmax 271 nm (ε=8,420). Paper chromatography (butanol/ethanol/water) showed a zone at $R_f$=0.04.

EXAMPLE 3

(a)

7-(α-Phenoxycarbonylphenylacetamido)-3-(1-methyl-1H-tetrazol-5-ylthio)methylceph-3-em-4-carboxylic acid

α-(Phenoxycarbonyl)phenylacetyl chloride (0.02 M) in dichloromethane (50 ml.) was added to 7-amino-3-(1-methyl-1H-tetrazol-5-ylthio)methylceph-3-em-4-carboxylic acid (6.56 g., 0.02 M) and triethylamine (6.0 ml.) in dichloromethane (100 ml.). The resulting solution was stirred at room temperature for three hours then the solvent was removed in vacuo, the residue dissolved in water (200 ml.) and washed with ethyl acetate (2×100 ml.). The aqueous solution was covered with ethyl acetate (50 ml.) acidified to pH 1.5 with 1 N hydrochloric acid, filtered, the organic phase was collected and the aqueous phase extracted with more ethyl acetate (50 ml.). The combined extracts were washed with water (2×100 ml.) and saturated sodium chloride (50 ml.) dried over anhydrous magnesium sulphate and evaporated to dryness in vacuo to give an oily residue which was triturated with anhydrous ether to give a pale brown solid (5.0 g.). This solid was dissolved in dilute sodium bicarbonate solution (100 ml.), treated with decolourising charcoal, filtered, acidified to pH 1.5 and the precipitated cephalosporin free acid collected and dried in vacuo.

Yield 4.53., 40.0%; N.M.R. spectrum [(CD$_3$)$_2$CO], δ=8.7-8.3 (1H,m, —NH—), 7.8-7.0 (10H,m, aromatic protons), 6.55 (1H,s, —CO$_2$H), 6.1-5.6 (1H,m, C$_7$ proton), 5.23 (1H,s, α-proton), 5.3-5.0 (1H,m, C$_6$ proton), 4.6-4.2 (2H,m, —CH$_2$S—), 3.98 (3H,s, tetrazole —CH$_3$), 4.0-3.3 (2H,m, C$_2$ methylene protons).

(b)

7-(α-Carboxyphenylacetamido)-3-(1-methyl-1H-tetrazol-5-ylthio)methyl-ceph-3-em-4-carboxylic acid disodium salt

7-(α-Phenoxycarbonylphenylacetamido)-3-(1-methyl-1H-tetrazol-5-ylthio)methylceph-3-em-4-carboxylic acid (4.53 g., 0.008 M) was dissolved in water (150 ml.) containing sodium tetraborate decahydrate (9.20 g., 0.024 M).

The resulting solution was stirred at room temperature for three hours, then acidified with 1 N hydrochloric acid to pH 4.0, washed with ethyl acetate (2×100 ml.), acidified to pH 1.8 and extracted with methylisobutylketone (2×100 ml.). The combined extracts were filtered, washed with water (2×50 ml.) and extracted to pH 6.5 with 1 N sodium bicarbonate solution. This aqueous extract was washed with ether (25 ml.) and freeze dried to give the cephalosporin disodium salt. Yield 2.78 g., 65.1%; N.M.R. spectrum (D$_2$O), δ=7.47 (5H,s, Ph-), 5.68 [1H,d, (J=4 Hz), C$_7$ proton], 5.3-4.9 (1H,m, C$_6$ proton), 4.6-3.8 (2H,m, —CH$_2$S—), 4.01 (3H,s, —CH$_3$), 3.8-3.3 (2H,m, C$_2$ methylene protons); U.V. spectrum (95% ethanol), λmax 273 nm (ε=8,665). Paper chromatography (butanol/ethanol/water) showed a zone at $R_f$=0.05.

EXAMPLE 4

7-(α-Carboxythien-2-ylacetamido)-3-(1-methyl-1H-tetrazol-5-ylthio)methylceph-3-em-4-carboxylic acid disodium salt

A suspension of thien-2-ylmalonic acid (0.93 g., 0.005 M) in water (25 ml.) was adjusted to pH 6.0 with saturated sodium bicarbonate solution, 7-amino-3-(1-methyl-1H-tetrazol-5-ylthio)methylceph-3-em-4-carboxylic acid was added, the solution again adjusted to 6.0, cooled to 0° and 1-(3-dimethylaminopropyl)-3-ethylcarbodiimide hydrochloride (1.01 g., 0.005 M) added. The mixture was maintained at pH 5.8–6.0 with 6 N hydrochloric acid for two hours at room temperature then saturated sodium bicarbonate was added to pH 7.7 and the solution washed with ethyl acetate (50 ml.). The solution was acidified to pH 4.0, washed with ethyl acetate (2×25 ml.), acidified to pH 2.0 and extracted with ethyl acetate (2×50 ml.), The extracts were washed with water (25 ml.) and brine (25 ml.), dried over anhydrous magnesium sulphate, treated with 2 N sodium 2-ethylhexoate in methylisobutylketone (2 ml.), diluted with ether (200 ml.) and the precipitated disodium salt collected and dried in vacuo. Yield 1.16 g., 43.0%; U.V. spectrum (95% ethanol), λmax (ε=8.250). Paper chromatography (butanol/ethanol/water) showed a zone at $R_f$=0.05.

EXAMPLE 5

(a)

7-(α-Phenoxycarbonylthien-3-ylacetamido)-3-(1H-1,2,4-triazol-3-ylthio)methylceph-3-em-4-carboxylic acid

7-Amino-3-(1H-1,2,4-triazol-3-ylthio)methylceph-3-em-4-carboxylic acid (1.45 g., 4.6 mmole) was suspended in anhydrous dichloromethane (15 ml.) containing pyridine (1.26 ml., 10.4 mmole) and N,O-bistrimethylsilylacetamide (1.86 ml., 10.4 mmole) and stirred at R.T. for one hour. Further N,O-bistrimethylsilylacetamide (1.0 ml.) was added and the mixture stirred for 30 minutes then cooled in an ice bath and treated dropwise with a solution of α-phenoxycarbonylthien-3-yl-acetyl chloride (5.0 mmole) in dichloromethane (15 ml.). The solution was stirred at room temperature for three hours then evaporated to dryness in vacuo and the residue dissolved in ethyl acetate (50 ml.) and water (50 ml.). The ethyl acetate was discarded, the aqueous solution was covered with ethyl acetate (25 ml.), acidified to pH 1.5 with N hydrochloric acid, the organic layer was collected and the aqueous phase extracted with more ethyl acetate (25 ml.). The combined extracts were washed with water (50 ml.) and saturated brine (25 ml.), dried over anhydrous magnesium sulphate, evaporated to dryness in vacuo and the residue triturated with anhydrous ether to give the cephalosporin free acid as a buff coloured solid.

Yield 1.28, 46.1%; N.M.R. spectrum [(CD$_3$)$_2$SO], δ=8.7-8.3 (1H,m, —NH—), 8.53 (1H,s, triazole —CH—), 8.1-7.0 (8H,m, aromatic and thienyl protons), 6.1-5.7 (1H,m, C$_7$ proton), 5.38 (1H,s, α-proton), 5.3-5.1 (1H,m, C$_6$ proton), 4.30 (2H,s, —CH$_2$S—), 4.0-3.5 (2H, m, C₂ methylene protons); U.V. spectrum (95% ethanol), λmax 269 nm (ε=7,940).

(b)

7-(α-Carboxythien-3-ylacetamido)-3-(1H-1,2,4-triazol-3-ylthio)-methylceph-3-em-4-carboxylic acid disodium salt 7-(α-Phenoxycarbonylthien-3-ylacetamido)-3-(1H-1,2,4-triazol-3-ylthio)methylceph-3-em-4-carboxylic acid (0.96 g.,) was dissolved in water (40 ml.) containing sodium tetraborate decahydrate (2.3 g.). The solution was stirred at room temperature for 2.5 hours, then acidified to pH 4.0 with N hydrochloric acid, washed with ethyl acetate (2×20 ml.), acidified to pH 2.0 and extracted with methyl isobutyl ketone (2×20 ml.). The extracts were washed with water (10 ml.) then extracted with N-sodium bicarbonate solution until the combined aqueous extract was at pH 7.0. The aqueous solution was washed with ether (20 ml.) and freeze dried to give the cephalosporin disodium salt, 0.56 g., 52.9% yield. U.V. spectrum (95% ethanol; λmax 269 nm (ε=5,560). Paper chromatography (n-butanol/ethanol/water) showed a zone at $R_f$=0.05.

EXAMPLE 6

(a)

7-(α-Phenoxycarbonylthien-3-ylacetamido)-3-(1-carboxymethyl-1H-tetrazol-5-ylthio)methylceph-3-em-4-carboxylic acid disodium salt 7-Amino-3-(1-carboxymethyl-1H-tetrazol-5-ylthio)-methylceph-3-em-4-carboxylic acid (1.86 g., 5.0 mmole) was dissolved in dichloromethane (50 ml.) containing triethylamine (5.5 ml.) and then α-phenoxycarbonylthien-3-ylacetyl chloride (7.5 mmole) in dichloromethane (20 ml.) was added in one portion. The mixture was stirred at room temperature for two hours then evaporated to dryness in vacuo and the residue dissolved in water (100 ml.), washed with ethyl acetate (2×25 ml.), and acidified to pH 1.5 in the presence of ethyl acetate (25 ml.). The mixture was filtered to remove the precipitate, the ethyl acetate was separated and the aqueous layer extracted with more ethyl acetate (2×20 ml.).

The combined extracts were washed with water (25 ml.) and saturated sodium chloride solution (20 ml.), dried over anhydrous magnesium sulphate, evaporated to dryness in vacuo and the residue triturated with ether to give a pale brown solid. This was suspended in water (20 ml.), adjusted to pH 6.0 with sodium bicarbonate solution, washed with ethyl acetate and the aqueous solution freeze dried to give the disodium salt, 0.78., 23.6% yield. U.V. spectrum (H₂O). λmax 266 nm (ε=18,000). T.l.c. on silica gel F254 eluted with n-butanol, acetic acid, water (12:3:5) showed a spot at $R_f$=0.35.

(b)

7-(α-Carboxythien-3-ylacetamido)-3-(1-carboxymethyl-1H-tetrazol-5-ylthio)methylceph-3-em-4-carboxylic acid trisodium salt 7-(α-Phenoxycarbonylthien-3-ylacetamido)-3-(1-carboxymethyl-1H-tetrazol-5-ylthio)methylceph-3-em-4-carboxylic acid disodium salt (0.7 g.) and sodium tetraborate decahydrate (0.76 g.) in water (25 ml.) were stirred at room temperature for three hours, washed with ether (2×25 ml.), acidified to pH 2.0 with N hydrochloric acid and extracted with ethyl acetate (3×15 ml.), The combined extracts were washed with water (10 ml.) then extracted to pH 6.5 with 0.3 N sodium bicarbonate solution. The bi-carbonate extract was washed with ether (20 ml.) and freeze dried to give a pale brown solid, 0.3 g., 50.9% yield. U.V. spectrum (H₂O), λmax 268 nm (ε=9,400). Paper chromatography (n-butanol/ethanol/water) showed a zone at the origin.

We claim:

1. A compound of formula (I) or a pharmaceutically acceptable salt or 4-carboxylic acid mono-ester thereof:

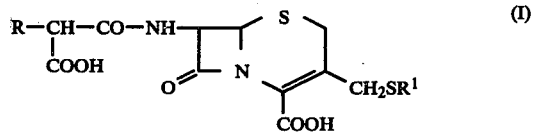

wherein R is 2- or 3-thienyl or phenyl or 4-hydroxyphenyl, and R¹ represents thiadiazolyl or tetrazolyl unsubstituted or substituted by lower alkyl.

2. A compound as claimed in claim 1 wherein R is 2- or 3-thienyl or phenyl.

3. A compound as claimed in claim 1 wherein R¹ represents 1,3,4-thiadiazolyl or 1,2,3,4-tetrazolyl unsubstituted or substituted by lower alkyl.

4. A compound as claimed in claim 3 wherein R¹ is 2-methyl-1,3,4-thiadiazol-5-yl or 1-methyl-1H-tetrazol-5-yl.

5. A compound as claimed in claim 1 in the form of its 4-carboxylic acid mono ester.

6. A compound as claimed in claim 5 wherein the ester is the acetoxymethyl, pivaloyloxymethyl, α-acetoxybenzyl, α-pivaloyloxyethyl, phthalidyl or 3,4-dimethoxyphthalidyl ester.

7. A compound as claimed in claim 1 which is 7-(α-carboxythien-3-ylacetamido)-3-(2-methyl-1,3,4-thiadiazol-5-ylthio)methylceph-3-em-4-carboxylic acid.

8. A compound as claimed in claim 1 which is 7-(α-carboxythien-3-ylacetamido)-3-(1-methyl-1H-tetrazol-5-ylthio)methylceph-3-em-4-carboxylic acid.

9. A compound as claimed in claim 1 which is 7-(α-carboxyphenylacetamido)-3-(1-methyl-1H-tetrazol-5-ylthio)methylceph-3-em-4-carboxylic acid.

10. A compound as claimed in claim 1 which is 7-(α-carboxythien-2-ylacetamido)-3-(1-methyl-1H-tetrazol-5-ylthio)methylceph-3-em-4-carboxylic acid.

* * * * *